US012606799B2

(12) United States Patent
Okazaki et al.

(10) Patent No.: US 12,606,799 B2
(45) Date of Patent: Apr. 21, 2026

(54) METHOD FOR DIRECT TRANSDIFFERENTIATION OF SOMATIC CELL

(71) Applicant: JUNTENDO EDUCATIONAL FOUNDATION, Bunkyo-ku (JP)

(72) Inventors: Yasushi Okazaki, Bunkyo-ku (JP); Masahito Matsumoto, Bunkyo-ku (JP); Hiroko Hagiwara, Bunkyo-ku (JP)

(73) Assignee: JUNTENDO EDUCATIONAL FOUNDATION, Bunkyo-ku (JP)

( * ) Notice: Subject to any disclaimer, the term of this patent is extended or adjusted under 35 U.S.C. 154(b) by 922 days.

(21) Appl. No.: 17/776,100

(22) PCT Filed: Nov. 12, 2020

(86) PCT No.: PCT/JP2020/042289
§ 371 (c)(1),
(2) Date: May 11, 2022

(87) PCT Pub. No.: WO2021/095811
PCT Pub. Date: May 20, 2021

(65) Prior Publication Data
US 2023/0220352 A1 Jul. 13, 2023

(30) Foreign Application Priority Data
Nov. 12, 2019 (JP) ................................. 2019-205015

(51) Int. Cl.
*C12N 5/071* (2010.01)
*C12N 5/077* (2010.01)
*C12N 5/0793* (2010.01)
*C12N 15/90* (2006.01)

(52) U.S. Cl.
CPC ........... *C12N 5/067* (2013.01); *C12N 5/0619* (2013.01); *C12N 5/0653* (2013.01); *C12N 5/0654* (2013.01); *C12N 5/0657* (2013.01); *C12N 15/907* (2013.01); *C12N 2500/02* (2013.01); *C12N 2501/11* (2013.01); *C12N 2501/115* (2013.01); *C12N 2501/119* (2013.01); *C12N 2501/12* (2013.01); *C12N 2501/165* (2013.01); *C12N 2501/33* (2013.01); *C12N 2506/1353* (2013.01)

(58) Field of Classification Search
None
See application file for complete search history.

(56) References Cited

U.S. PATENT DOCUMENTS

| | | |
|---|---|---|
| 2011/0112015 A1 | 5/2011 | Julier et al. |
| 2013/0029423 A1 | 1/2013 | Yamanaka et al. |
| 2015/0166958 A1 | 6/2015 | Kishida et al. |
| 2016/0153000 A1* | 6/2016 | Glorioso .................. A61P 9/00 435/456 |
| 2016/0160180 A1 | 6/2016 | Yamamoto et al. |
| 2017/0002319 A1 | 1/2017 | D'Alessio et al. |
| 2017/0211046 A1 | 7/2017 | Matsumoto et al. |
| 2018/0312812 A1* | 11/2018 | Matsumoto et al. |
| 2020/0399603 A1 | 12/2020 | Kishida et al. |
| 2022/0401488 A1* | 12/2022 | Kenderian ....... A61K 39/00113 |

FOREIGN PATENT DOCUMENTS

| | | |
|---|---|---|
| JP | 2009-533047 A | 9/2009 |
| JP | 2013-519371 A | 5/2013 |
| JP | 2018-108080 A | 7/2018 |
| WO | WO 2015/012377 A1 | 1/2015 |
| WO | WO 2016/002937 A1 | 1/2016 |
| WO | WO 2017/073740 A1 | 5/2017 |

OTHER PUBLICATIONS

Berkman (printout from https://www.genome.gov/genetics-glossary/Substitution#:~:text=Changing a single nucleotide will, forms will look and act. pp. 1-4, 2025) (Year: 2025).*
Lichti-Kaiser et al. Vitam Horm 2012 88:141-171; printed pp. 1-27 of Author Manscript (Year: 2012).*
Leri et al. Circ Res 2015 116:150-166 (Year: 2015).*
International Search Report issued Jan. 19, 2021 in PCT/JP2020/042289 filed on Nov. 12, 2020, 3 pages.
Chao et al., "Human retinal pigment epithelial cells prefer proline as a nutrient and transport metabolic intermediates to the retinal side", J. Biol. Chem., 2017, vol. 292(31), pp. 12895-12905.
Sui et al., "Role of BMP Signaling in Pancreatic Progenitor Differentiation from Human Embryonic Stem Cells", Stem Cell Rev and Rep, 2013, vol. 9(5), pp. 569-577.
Maekawa et al., "Direct reprogramming of somatic cells is promoted by maternal transcription factor Glis1", Nature, 2011, vol. 474(7350), pp. 225-229 (6 total pages).
Yasuoka et al., "Evolutionary History of *GLIS* Genes Illuminates Their Roles in Cell Reprogramming and Ciliogenesis", Mol. Biol. Evol., Sep. 5, 2019, vol. 37(1), pp. 100-109.
Extended European Search Report issued Nov. 14, 2023 in Patent Application No. 20886657.4, 9 pages.
Konno M. et al., "Adipose-derived mesenchymal stem cells and regenerative medicine," Development, Growth & Differentiation, vol. 55, 2013, XP071144107, pp. 309-318.
Japanese Office Action Issued Nov. 12, 2024 in Japanese Patent Application No. 2021-556151 (with unedited computer-generated English translation). 16 pages.

* cited by examiner

*Primary Examiner* — Marcia S Noble
(74) *Attorney, Agent, or Firm* — Oblon, McClelland, Maier & Neustadt, L.L.P.

(57) ABSTRACT

A method of direct transdifferentiation of somatic cells into other somatic cells may be convenient and still have good reproducibility, excellent production efficiency, and short performed time. Methods for direct transdifferentiation of somatic cells into other somatic cells may include: (a) introducing a GLIS family gene, a mutated GLIS family gene or a gene product thereof into somatic cells; and (b) culturing the gene-introduced somatic cells in a culture medium containing a component that induces differentiation of the somatic cells or precursor cells of the somatic cells into other somatic cells.

2 Claims, 5 Drawing Sheets
Specification includes a Sequence Listing.

A: GFP CTL

B: K1(#14)

C: K2(Ert) 4OH(-)

D: K2(Ert) 4OH(+)

*K1(Full length),K2(ΔN)
*x 100

Green: Tuj-1(Neuron marker)
Blue: DAPI

△ : Neuronal cell-like cells

2w after induction of Neurogenic cells

Figure 3

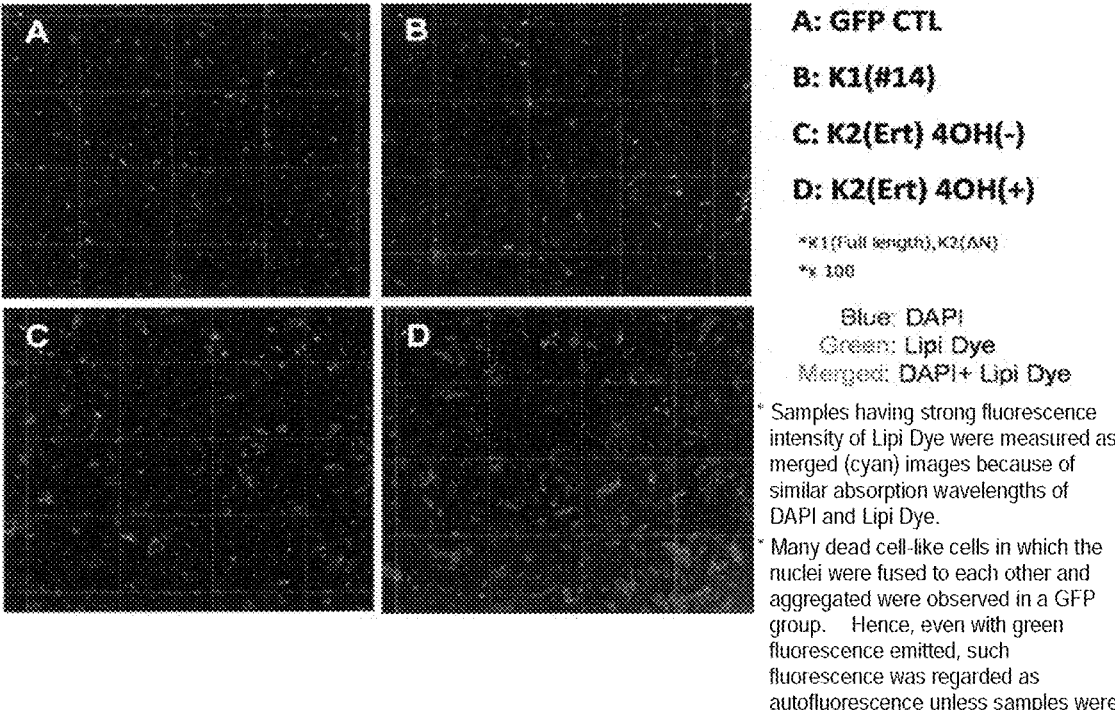

A: GFP CTL

B: K1(#14)

C: K2(Ert) 4OH(-)

D: K2(Ert) 4OH(+)

**K1(Full length), K2(ΔN)
*x 100

Blue: DAPI
Green: Lipi Dye
Merged: DAPI+ Lipi Dye

* Samples having strong fluorescence intensity of Lipi Dye were measured as merged (cyan) images because of similar absorption wavelengths of DAPI and Lipi Dye.
* Many dead cell-like cells in which the nuclei were fused to each other and aggregated were observed in a GFP group.   Hence, even with green fluorescence emitted, such fluorescence was regarded as autofluorescence unless samples were in a lipid droplet form; thus measurement was not performed.

Figure 4

2w after of Adipogenic cells

***: v.s. GFP , p>0.005
†: K1#14v.s. K2(Ert)#9 (4-OH(+)), p> 0.005

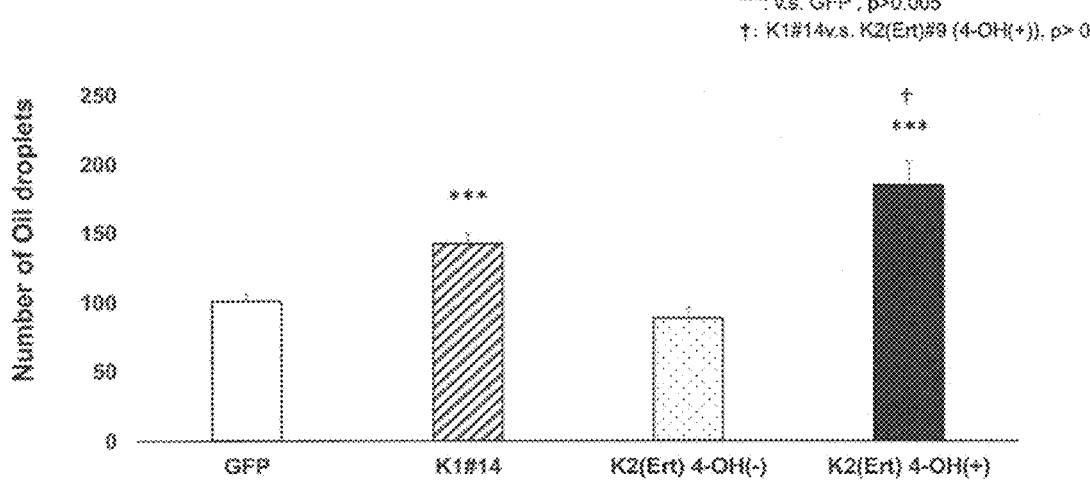

Figure 5
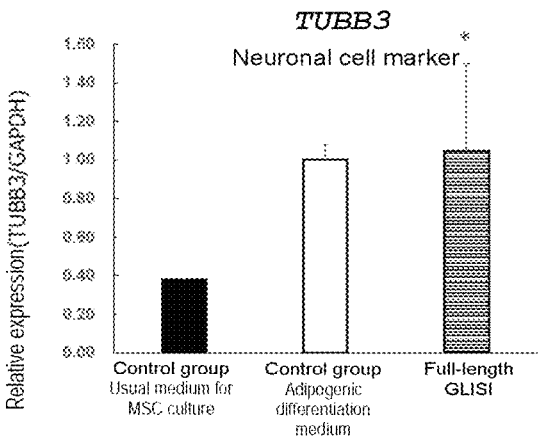
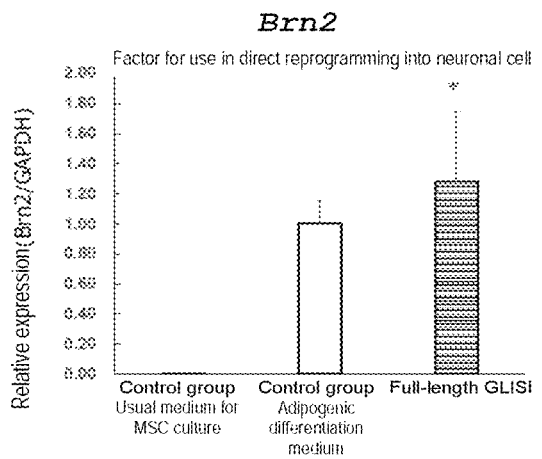
Figure 6
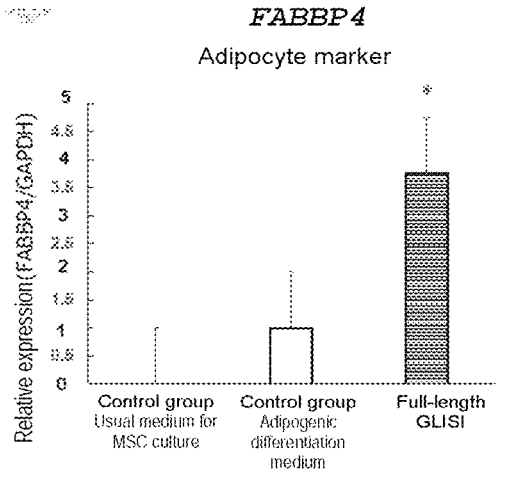
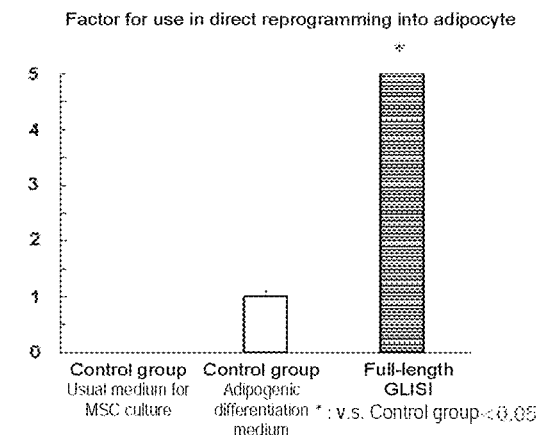
Figure 7
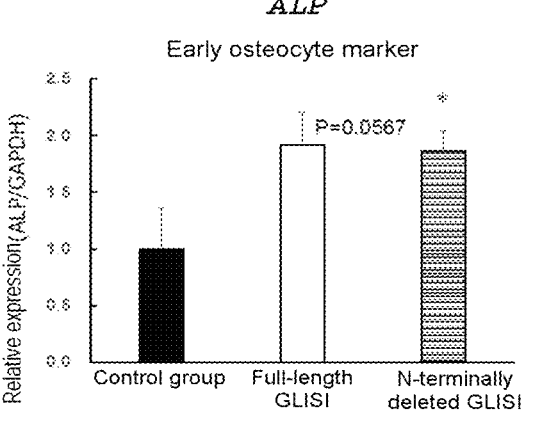
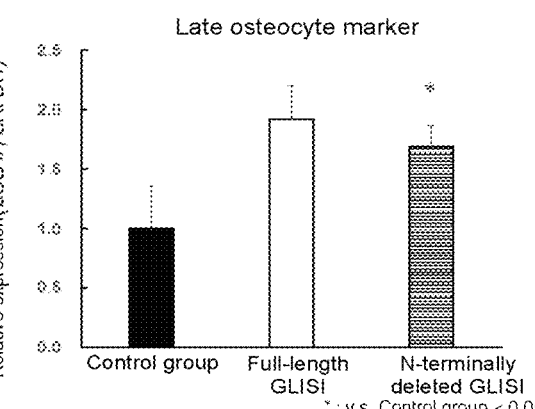

Cardiomyogenic Differentiation-inducing factor     : *Tbx5, Mef2c, GATA4*  (Ieda.M et al.(2010) )

Cardiomyogenic differentiaio-inducing factor     : *Tbx5, Mef2c, GATA4, Hand2*   (Muraoka.N et al.(2019) )

Astrogenic differentiation- inducing factor   : *HNF4a, FOXA3*  (Suzuki.A et al.(2011) )

SEQUENCE LISTING

```
<160> NUMBER OF SEQ ID NOS: 36

<210> SEQ ID NO 1
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggttgccg gtcggcaggc atgccgctgg gtggactgct gcgcagccta cgagcagcag       60
gaggagctgg tgcggcacat cgagaagagc cacatcgacc agcgcaaggg cgaagacttc      120
acctgcttct gggccgggtg tgtgcggcgc tacaagccct tcaatgcccg ctacaagctg      180
ctcatccaca tgagggtaca ctcaggcgag aagcccaaca agtgcatgtt cgaaggctgc      240
agtaaagcct tttcccgtct ggagaacctg aagatccatc tgcggagcca cacaggcgag      300
aaaccatacc tgtgccagca cccaggctgc cagaaggcct tcagcaactc cagcgaccgt      360
gccaagcacc aacgcaccca cctcgacacg aagccatatg cttgtcagat ccctggctgc      420
tccaagcgct acacggaccc cagctccctc cgcaagcacg tgaaggccca ctcagccaaa      480
gagcagcagg tgcgtaagaa gctgcacaca ggtgccgacc cagaggctga tgttctgtcc      540
gagtgtctgt ccctgcagca gctccaagca tccacactgt tgccggccag cagagggaag      600
ggcagccaaa ccctgagcca ggagctcctc ccaggtgtgt atcctggctc cgtcacccca      660
caaaacgggc ttgcttcagg catcctgtcc ccctcccacg atgtcccttc caggcaccac      720
ccactggagg tccccactgg ttcccaccac cacctgtccc ctctgcccac agctgagagc      780
accagggatg gcctgggggcc cagtctcctt tcacccatgg tcagcccact gaaggggctt      840
ggtcccccac cgctaccacc agcctcccag agtcagtctc caggggggaca gtcattctct      900 acagtcccca gcaagcctac ctacccatcc ttccaaagcc caccacctct gcccagcccc      960
caaggctacc aaggcagttt ccattccatc cagaactgct tcccctacgc tgactgctac     1020
cgggccactg agccagcagc ctccagggat ggactggtgg gtgatgccca cggtttcaac     1080
cccttgcgac ccagcacata ctccagcctc agcacacctt tatccgcacc aggctacgag     1140
```

-continued

```
accctggcag aaacgccgtg tcccccagcg ctgcagccac agccagctga agacctggta      1200
cctagtggtc ctgaggactg tggcttcttc cccaatgggg cctttgacca ctgtctgagt      1260
cacatcccgt ccatctacac tgacacctga                                       1290

<210> SEQ ID NO 2
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggtggtgg ccgggcggca ggcgtgccgc tgggtggact gctgtgcagc ctatgagcag        60
caggaggagc tggtgcggca catcgagaag agccacatcg accagcgcaa gggcgaggac       120
ttcacctgct tctgggctgg ctgcgtgcgc cgctacaagc ccttcaacgc ccgctacaag       180
ctgctcatcc acatgcgagt gcactcgggc gagaagccca acaagtgcat gtttgaaggc       240
tgcagcaagg ccttctcacg gctggagaac ctcaagatcc acctgaggag ccacacgggc       300
gagaagccgt acctgtgcca gcacccgggt tgccagaagg ccttcagcaa ctccagcgac       360
cgcgccaagc accagcgcac ccacctagac acgaagccgt acgcctgtca gatccctggc       420
tgctccaagc gctacacaga ccccagctcc ctccgcaagc acgtcaaggc ccattcagcc       480
aaagagcagc aggtgcgtaa gaagctgcat gcgggccctg acaccgaggc cgacgtcctg       540
accgagtgtc tggtcctgca gcagctccac acgtccacac agctggctgc cagcgacggc       600
aagggtggct gtggcctggg ccaggagctg ctcccaggtg tgtatcctgg ctccatcacc       660
ccccataacg gacttgcatc gggcctcctg ccccagcgc acgacgtacc ttccaggcac       720 caccgctgg atgccaccac cagttcccac caccatctgt ccctctgcc catggctgag        780 agcacccggg atgggttggg gcccggcctc ctctcaccaa tagtcagccc cctgaagggg       840
ctggggccac cgccgctgcc cccatcctct cagagccatt ctccggggg ccagcccttc        900 cccacactcc ccagcaagcc gtcctaccca cccttccaga gccctccacc cccgcctctg       960
cccagcccac aaggttacca gggcagtttc cactccatcc agagttgctt ccctatggc       1020 gactgctacc ggatggctga accagcagcc ggtggggacg gactggtcgg ggagacccac      1080
ggtttcaacc ccctgcggcc caatggctac cacagcctca gcacgccctt gcctgccaca      1140
ggctatgagg ccctggctga ggcctcatgc cccacagcgc tgccacagca gccatctgaa      1200
gatgtggtgt ccagcggccc cgaggactgt ggcttcttcc ccaatggagc ctttgaccac      1260
tgcctgggcc acatcccctc catctacaca gacacctga                            1299

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cactgacttt tgctgctgct tct                                               23

<210> SEQ ID NO 4
<211> LENGTH: 15
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 4
tggcgctcgc gtgtg                                                      15

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcaaaaggaa agcaactaag ac                                              22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatctctct gtctctctct c                                               21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttgttaaacc tcggcaaaat cg                                              22

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agactattgg aggtattgct gttcatt                                         27

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccaagttc tgggaagtca                                                 20

<210> SEQ ID NO 10
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 10
cgagtcgccc acgtagttg                                                    19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tctcaaacga gagtcagcct tt                                                22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcaggctcca ctttgattgc                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tactgggcca ggaatttgac                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtggaagtga cgcctttcat                                                   20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
catgctgagt gacacagaca agaag                                             25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
tggtagttgt tgtgagcata gtcca                                          25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctcacactc ctcgccctat                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcttggaca caaaggctgc                                                20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcaacattt ccaatccgac cc                                             22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggcatccttg ctcttagtgg g                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcggtagaac agttgacaga g                                              21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 22
ccagctcctt ggtgctgat                                                    19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atggccgata cagatgaggg                                                   20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttcgtggaac ttggggtgtc t                                                 21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcccagtatc acaggccac                                                    19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgggcttcca gaaccaaga                                                    19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccctacccag cctacatgg                                                    19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 28
ccacatccat ctccacgtgg                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaaaccaacc tgaggctgga                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccacatccat ctccacgtgg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctcctctct ctccctctcg                                              20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggggcagaag tgcttcaat                                               19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aacctttggc attgtggaag g                                            21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
```

```
                                          -continued acacattggg ggtaggaaca                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atgttcgtca tgggtgtgaa                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgtggtcatg agtccttcca                                              20
```

METHOD FOR DIRECT TRANSDIFFERENTIATION OF SOMATIC CELL

CROSS-REFERENCE TO RELATED APPLICATIONS

The present application is the national stage of international application PCT/JP2020/042289, filed on Nov. 12, 2020, and claims the benefit of the filing date of Japanese Appl. No. 2019-205015, filed on Nov. 12, 2019.

SEQUENCE LISTING

The instant application contains a Sequence Listing which has been submitted electronically in ASCII format and is hereby incorporated by reference in its entirety. Said ASCII copy, created on Jun. 30, 2022, is named 543033US_SL.txt and is 12,066 bytes in size.

TECHNICAL FIELD

The present invention relates to a method for production by direct transdifferentiation of somatic cells into another somatic cells.

BACKGROUND ART

Somatic cells such as adipocytes, neuronal cells, cardiomyocytes, and hepatocytes are expected to be used as materials of regenerative medicine and, for example, as materials for use in the screening of diseases involving these cells. Hence, there is a strong demand for the development of methods for preparing these somatic cells at a large scale in vitro.

Methods for producing these somatic cells using embryonic stem cells (hereinafter, also referred to as "ES cells") or induced pluripotent stem cells (hereinafter, also referred to as "iPS cells") have been proposed. However, the methods require creating a cultural environment, for example, by adding various inhibitors involved in development and differentiation to a cell culture medium and thus have problems associated with complication. Another problem thereof is that reproducibility may not be obtained. The methods also produce cells other than the somatic cells of interest and thus have problems associated with efficiency. The methods further require at least 21 days to 30 days for obtaining the somatic cells of interest and thus cannot produce these cells in a short period of time, leading to further problems.

For adipocytes, for example, among these somatic cells, methods for inducing differentiation by culturing fibroblasts, mesenchymal stem cells or precursor cells of these somatic cells in a culture medium containing a component involved in a transcription factor have also been reported. However, these methods for inducing differentiation have low induction efficiency of differentiation and thus have problems associated with efficiency. Hence, any of the methods have not yet been adopted as a large-scale approach of preparing the somatic cells.

GLIS1 (GLIS family zinc finger 1), which belongs to the GLIS family, is known to improve the establishment efficiency of iPS cells (see e.g., Patent Literature 1). It is also known that GLIS3 (GLIS family zinc finger 3) can be used for inducing the differentiation of human multipotent or pluripotent cells into functional pancreatic β cells that produce insulin (see e.g., Patent Literature 2).

The present inventors have filed patent applications, based on the finding that somatic cells can be directly transdifferentiated into pancreatic endocrine cells by introducing a GLIS family gene and a neurogenin 3 gene into the somatic cells or by introducing a GLIS family gene, a neurogenin 3 gene, and a Pdx1 gene into the somatic cells (Patent Literatures 3 and 4).

However, it has been totally unknown that the GLIS family gene such as GLIS1 is involved alone in direct conversion of somatic cells into another somatic cells except for pancreatic endocrine cells without undergoing the stem cell stage.

CITATION LIST

Patent Literature

Patent Literature 1: JP-A-2013-519371
Patent Literature 2: JP-A-2009-533047
Patent Literature 3: WO 2016/002937
Patent Literature 4: WO 2017/073740

SUMMARY OF INVENTION

Technical Problem

An object of the present invention is to provide a method for production by direct transdifferentiation of somatic cells into another somatic cells, which is convenient, has good reproducibility, is excellent in production efficiency, and is performed in a short period of time.

Solution to Problem

Accordingly, the present inventors have conducted various studies on what action a GLIS family gene alone has on the transdifferentiation of somatic cells, and consequently found that, totally unexpectedly, the transdifferentiation efficiency of somatic cells into another somatic cells is drastically improved by culturing somatic cells into which a GLIS family gene has been introduced in a culture medium containing a component that induces differentiation of the somatic cells. It has also been found that the transdifferentiation efficiency of somatic cells into another somatic cells is drastically improved by culturing somatic cells into which a GLIS family gene and a transcription factor have been introduced in a culture medium containing a growth factor of the somatic cells. On the basis of these findings, the present invention has been completed.

Specifically, the present invention provides the following [1] to [14].

[1] A method for production by direct transdifferentiation of somatic cells into another somatic cells, comprising:
　(a) a step of introducing a GLIS family gene, a mutated GLIS family gene or a gene product thereof into somatic cells; and
　(b) a step of culturing the gene-introduced somatic cells in a culture medium containing a component that induces differentiation of the somatic cells or precursor cells of the somatic cells into another somatic cells.

[2] A method for production by direct transdifferentiation of somatic cells into another somatic cells, comprising:
　(c) a step of introducing a GLIS family gene, a mutated GLIS family gene or a gene product thereof and a transcription factor into somatic cells; and (d) a step of culturing the gene-introduced somatic cells in a culture medium containing a growth factor of another somatic cells.

[3] The method for production according to [1] or [2], wherein the GLIS family gene is GLIS1 gene.

[4] The method for production according to any of [1] to [3], wherein the mutated GLIS family gene is a gene encoding a protein in which some of amino acid residues at N-terminus of a GLIS1 protein have been deleted.

[5] The method for production according to any of [1] to [4], wherein the mutated GLIS family gene is a gene encoding a protein in which 100 to 360 amino acid residues at N-terminus of the GLIS1 protein have been deleted.

[6] The method for production according to any of [1] to [5], wherein the somatic cells are fibroblasts or mesenchymal stem cells.

[7] The method for production according to any of [1] to [6], wherein the another somatic cells are selected from the group consisting of adipocytes, neuronal cells, cardiomyocytes, hepatocytes, osteocytes and blood cells.

[8] Somatic cells obtained by the method for production according to any of [1] to [7].

[9] The somatic cells according to [8], wherein the somatic cells are selected from the group consisting of adipocytes, neuronal cells, cardiomyocytes, hepatocytes, osteocytes and blood cells.

[10] An agent for promoting direct transdifferentiation of somatic cells into another somatic cells, comprising a GLIS family gene, a mutated GLIS family gene or a gene product thereof.

[11] The agent for promoting direct transdifferentiation of somatic cells into another somatic cells according to [10], wherein the somatic cells are fibroblasts or mesenchymal stem cells, and the another somatic cells are selected from the group consisting of adipocytes, neuronal cells, cardiomyocytes, hepatocytes, osteocytes and blood cells.

[12] An agent for direct transdifferentiation of somatic cells into another somatic cells, comprising a GLIS family gene, a mutated GLIS family gene or a gene product thereof, and a component that induces differentiation of somatic cells into another somatic cells.

[13] An agent for direct transdifferentiation of somatic cells into another somatic cells, comprising a GLIS family gene, a mutated GLIS family gene or a gene product thereof, a transcription factor, and a growth factor of another somatic cells.

[14] The agent for direct transdifferentiation of somatic cells into another somatic cells according to [13], wherein the somatic cells are fibroblasts or mesenchymal stem cells, and the another somatic cells are selected from the group consisting of adipocytes, neuronal cells, cardiomyocytes, hepatocytes, osteocytes and blood cells.

Advantageous Effects of Invention

According to the present invention, the direct transdifferentiation of somatic cells into another somatic cells can be achieved conveniently in a short period of time with good reproducibility and excellent production efficiency. This enables somatic cells to be supplied as materials of regenerative medicine and to be supplied as research materials for various diseases.

BRIEF DESCRIPTION OF DRAWINGS

FIG. 3 shows Lipi Dye staining images of adipocytes after culture for 2 weeks. Green and cyan (light blue) portions are the stain portions of lipid droplets in the adipocytes stained with Lipi Dye. GFP depicts a control. K1 #14 depicts results of culturing the cells in a culture medium containing a differentiation-inducing component after GLIS1 gene introduction. K2 #9(4-OH(−)) depicts results of culturing the cells in a culture medium containing a differentiation-inducing component after mutated GLIS1 gene introduction. K2(Ert) #9(4-OH(+)) depicts results of culturing the cells in a culture medium containing a differentiation-inducing component and an estrogen receptor antagonist after mutated GLIS1 gene introduction.

FIG. 4 is a graph showing induction efficiency into adipocytes after culture for 2 weeks. GFP depicts a control. K1 #14 depicts results of culturing the cells in a culture medium containing a differentiation-inducing component after GLIS1 gene introduction. K2 #9(4-OH(−)) depicts results of culturing the cells in a culture medium containing a differentiation-inducing component after mutated GLIS1 gene introduction. K2(Ert) #9(4-OH(+)) depicts results of culturing the cells in a culture medium containing a differentiation-inducing component and an estrogen receptor antagonist after mutated GLIS1 gene introduction.

FIG. 5 is graphs showing induction efficiency into neuronal cells after culture for 2 weeks. The left graph shows change in the expression level of a neuronal cell marker (TUBB3). The right graph shows change in the expression level of a neurogenic differentiation-inducing component (Brn2).

FIG. 6 is graphs showing induction efficiency into adipocytes after culture for 2 weeks. The left graph shows change in the expression level of an adipocyte marker (FABP4). The right graph shows change in the expression level of an adipogenic differentiation-inducing component (PPARγ).

FIG. 7 is graphs showing induction efficiency into osteocytes after culture for 2 weeks. The left graph shows change in the expression level of an early osteocyte marker (ALP). The right graph shows change in the expression level of an osteogenic differentiation-inducing component (BGLAP).

DESCRIPTION OF EMBODIMENTS

Figure 1:
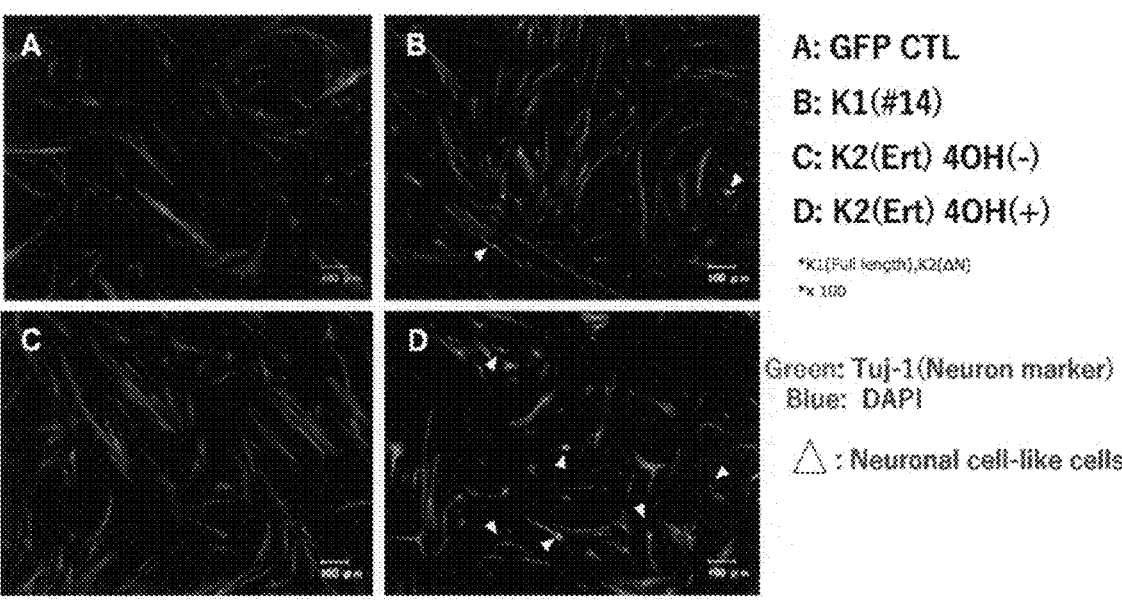
FIG. 1 shows neural marker (Tuj-1) immunostaining images of changes in neuronal cell differentiation over time from 1 week to 3 weeks after the start of induction of differentiation. GFP depicts a control. K1 #14 depicts results of culturing the cells in a culture medium containing a differentiation-inducing component after GLIS1 gene introduction. K2 #9(4-OH(−)) depicts results of culturing the cells in a culture medium containing a differentiation-inducing component after mutated GLIS1 gene introduction. K2(Ert) #9(4-OH(+)) depicts results of culturing the cells in a culture medium containing a differentiation-inducing component and an estrogen receptor antagonist after mutated GLIS1 gene introduction.

A first embodiment of the method for direct transdifferentiation of somatic cells into another somatic cells of the present invention includes the following steps (a) and (b):

(a) a step of introducing a GLIS family gene, a mutated GLIS family gene or a gene product thereof into somatic cells; and (b) a step of culturing the gene-introduced somatic cells in a culture medium containing a component that induces differentiation of the somatic cells or precursor cells of the somatic cells into another somatic cells.

The GLIS family gene for use in the step (a) is not particularly limited and can be appropriately selected for any purpose. Examples thereof include GLIS1, GLIS2, and GLIS3. One of these genes may be used alone, or two or more thereof may be used in combination. Among the members of the GLIS family, GLIS1 and GLIS3 are preferred, and GLIS1 is more preferred, because of being excellent in an effect of improving the direct transdifferentiation efficiency of the somatic cells into another somatic cells.

The origin of the GLIS family gene is not particularly limited and can be appropriately selected for any purpose. Examples thereof include humans and mice.

Sequence information on the GLIS family gene can be obtained from a database known in the art and can be obtained, for example, from NCBI accession Nos NM 147193 (human GLIS1), NM_147221 (mouse GLIS1), NM_032575 (human GLIS2), NM_031184 (mouse GLIS2), NM_152629 (human GLIS3), NM_175459, and NM_172636 (mouse GLIS3).

The mutated GLIS family gene for use in the step (a) is a mutant of the GLIS family gene, preferably a mutant of the GLIS1 gene, more preferably a gene encoding a protein in which some of amino acid residues at N-terminus of the GLIS1 protein are deleted, further more preferably a gene encoding a protein in which 100 to 360 amino acid residues at N-terminus of the GLIS1 protein are deleted. Specifically, examples thereof include a gene having 85% or higher sequence identity to the nucleotide sequence represented by any of SEQ ID NOs: 1 and 2.

The nucleotide sequence represented by SEQ ID NO: 1 is the sequence of a gene encoding a protein in which 360 amino acid residues at N-terminus of the mouse GLIS1 protein are deleted.

The nucleotide sequence represented by SEQ ID NO: 2 is the sequence of a gene encoding a protein in which 190 amino acid residues at N-terminus of the human GLIS1 protein are deleted.

The sequence identity to the nucleotide sequence represented by any of SEQ ID NOs: 1 and 2 is not particularly limited as long as the sequence identity is 85% or higher. The sequence identity can be appropriately selected for any purpose and is preferably 90% or higher, more preferably 95% or higher, further more preferably 98% or higher, particularly preferably 99% or higher.

The method for determining the sequence identity is not particularly limited, and a method known in the art can be appropriately selected. The sequence identity can be determined using, for example, algorithm BLAST by Karlin and Altscul (Karlin, S. & Altschul, S. F. (1990) Proc. Natl. Acad. Sci. USA 87: 2264-2268; and Karlin, S. & Altschul, S. F., Proc. Natl. Acad. Sci. USA 90: 5873).

The gene product refers to mRNA transcribed from a gene or a protein translated from the mRNA. Examples of the gene product used in the present invention include mRNA transcribed from the GLIS family gene, a protein translated from the mRNA, mRNA transcribed from the mutated GLIS family gene, and a protein translated from the mRNA.

The sequence of the GLIS family gene, the mutated GLIS family gene or the gene product thereof may be in a form consisting of a portion to be translated into a protein, of the sequence of each of the genes, or may be in a form comprising a portion other than the portion to be translated into a protein.

In the step (a), the cells into which the gene or the gene product is to be introduced are somatic cells. The somatic cells are not particularly limited and can be appropriately selected for any purpose. The somatic cells may be undifferentiated precursor cells or may be mature cells after final differentiation. The somatic cells may be derived from ES cells or derived from iPS cells and is preferably mature cells derived from somatic cells or precursor cells of the somatic cells of interest.

Specific examples of the somatic cells include adipose tissue-derived stromal (stem) cells, mesenchymal stem cells, and fibroblasts. Among them, fibroblasts or a mesenchymal stem cells are preferred.

The species of an individual from which the somatic cells are collected is not particularly limited and can be appropriately selected for any purpose. Examples thereof include humans and mice.

The individual from which the somatic cells are collected is not particularly limited and can be appropriately selected for any purpose. In the case of using another somatic cells of interest for a regenerative medicine purpose, the individual itself or another individual having the same type or substantially the same type of MHC as that of the individual is preferred from the viewpoint of rejection reaction. In this context, the phrase "substantially the same type of MHC" means that the type of MHC is compatible to the extent that, when transplanting another somatic cells derived from the somatic cells to an individual, the transplanted cells are capable of being engrafted with use of immunosuppressant or the like. The time when the somatic cells are collected from the individual is not particularly limited and can be appropriately selected for any purpose.

The culture conditions of the somatic cells are not particularly limited and can be appropriately selected for any purpose. For example, the culture temperature is approximately 37° C. Examples of the $CO_2$ concentration include approximately 2% to 5%. The culture medium for use in the culture of the somatic cells is not particularly limited and can be appropriately selected for any purpose. Examples thereof include minimum essential medium (hereinafter, also referred to as "MEM"), Dulbecco's modified Eagle medium (hereinafter, also referred to as "DMEM"), RPMI1640 medium, 199 medium, and F12 medium, containing 5% by mass to 20% by mass of serum.

The method for introducing each of the genes or the gene product thereof into the somatic cells in the step (a) is not particularly limited and can be appropriately selected for any purpose. Examples thereof include a method using a vector, a method using synthesized mRNA (messenger RNA), and a method using a recombinant protein.

The vector is not particularly limited and can be appropriately selected for any purpose. Examples thereof include viral vectors and non-viral vectors.

Specific examples of the virus vector include retrovirus vectors and lentivirus vectors. Specific examples of the non-viral vector include plasmid vectors and episomal vectors.

The method for introducing the vector into the somatic cells is not particularly limited, and a method known in the art can be appropriately selected for any purpose. In the case of using, for example, the retrovirus vector, the method described in WO 2007/69666, Cell, 126, 663-676 (2006), Cell, 131, 861-872 (2007), etc. can be used. In the case of using the lentivirus vector, the method described in Science, 318, 1917-1920 (2007), etc. can be used. In the case of using the plasmid vector, the method described in Science, 322, 949-953 (2008), etc. can be used. In the case of using the episomal vector, the method described in Science, 324: 797-801 (2009), Biochemical and Biophysical Research Communications, 426: 141-147 (2012), etc. can be used.

In the case of using the virus vector, virus particles obtained using packaging cells may be used. The packaging cells are cells into which a gene encoding a viral structural protein has been introduced. When a recombinant virus vector with a gene of interest incorporated thereinto is introduced into the cells, recombinant virus particles into which the gene of interest has been incorporated is produced.

The packaging cells are not particularly limited and can be appropriately selected for any purpose. Examples thereof include packaging cells based on human kidney-derived HEK293 cells or mouse fibroblast-derived NIH3T3 cells, packaging cells Platinum-E (hereinafter, also referred to as "Plat-E cells") which are allowed to express viral structural proteins gag-pol and env under the control of MoMuLV (Moloney murine leukemia virus) LTRs (long terminal repeats) and can produce high-titer viruses over a long period of time, PLAT-A cells designed so as to express an amphotropic virus-derived envelope glycoprotein, and PLAT-GP cells designed so as to express a vesicular stomatitis virus-derived envelope glycoprotein.

The method for introducing the virus vector into the packaging cells is not particularly limited and can be appropriately selected for any purpose. Examples thereof include lipofection, electroporation, and a calcium phosphate method. The method for infecting the somatic cells with the obtained virus particles is not particularly limited and can be appropriately selected for any purpose. Examples thereof include a polybrene method.

The vector may contain a marker gene for confirming that each of the genes has been introduced. The marker gene refers to a gene that allows screening or selection of cells by introducing the marker gene into the cells. Specific examples of the marker gene include drug resistance genes, fluorescent protein genes, luminescent enzyme genes, and chromogenic enzyme genes. One of these marker genes may be used alone, or two or more thereof may be used in combination.

Specific examples of the drug resistance gene include neomycin resistance gene, tetracycline resistance gene, kanamycin resistance gene, zeocin resistance gene, and hygromycin resistance gene.

Specific examples of the fluorescent protein gene include green fluorescent protein (GFP) gene, yellow fluorescent protein (YFP) gene, and red fluorescent protein (RFP) gene.

Specific examples of the luminescent enzyme gene include luciferase gene.

Specific examples of the chromogenic enzyme gene include β galactosidase gene, β glucuronidase gene, and alkaline phosphatase gene.

The method for introducing the mRNA into the somatic cells is not particularly limited, and a method known in the art can be appropriately selected and used.

The method for introducing the recombinant protein into the somatic cells is not particularly limited, and a method known in the art can be appropriately selected and used.

The number of times of introduction of each of the genes or the gene product thereof into the somatic cells is not particularly limited and can be appropriately selected for any purpose. The number of times may be one or may be two or more.

A time when each of the genes or the gene product thereof is introduced into the somatic cells is not particularly limited and can be appropriately selected for any purpose. All the genes or the gene products thereof may be introduced at the same time or may be introduced at different times.

The amount of each of the genes or the gene product thereof to be introduced into the somatic cells is not particularly limited and can be appropriately selected for any purpose. All the genes or the gene products thereof may be introduced in equal amounts or introduced in different amounts.

The gene or the gene product of a gene may be in a form using only the gene, may be in a form using only the gene product, or may be in a form using both of the gene or the gene product thereof. The combination with different genes or gene products thereof is not particularly limited and can be appropriately selected for any purpose. For each of the genes or gene products, the same or different forms may be used. In the step of introducing the gene or the gene product thereof, a material other than the gene or the gene product thereof may be introduced without impairing the advantageous effects of the present invention.

Next, the step (b) will be described. The step (b) is the step of culturing the gene-introduced somatic cells in a culture medium containing a component that induces differentiation of the somatic cells or precursor cells of the somatic cells into another somatic cells (also referred to as the somatic cells of interest).

The combination of the starting material somatic cells and the somatic cells of interest in the step (b) is not particularly limited. The starting material somatic cells are preferably the fibroblasts or the mesenchymal stem cells. In this context, the mesenchymal stem cells are preferably bone marrow-derived stem cells.

Examples of the somatic cells of interest include adipocytes, neuronal cells, cardiomyocytes, hepatocytes, osteocytes and blood cells. The blood cells are particularly preferably white blood cells or red blood cells.

The component contained in the culture medium for use in the step (b) is a component that induces differentiation of the somatic cells or precursor cells of the somatic cells into another somatic cells (also referred to as the somatic cells of interest). A component known for each somatic cell of interest can be used as such a component that induces differentiation.

3-Isobutyl-1-methylxanthine (IBMX), dexamethasone (DEX), insulin, and the like are known as a component that induces differentiation of fibroblasts or mesenchymal stem cells into adipocytes. These components can be used alone or in combination of two or more. Among these components, 3-isobutyl-1-methylxanthine (IBMX), dexamethasone (DEX) and insulin are particularly preferably used.

EGF (epithelial growth factor), FGF-2 (fibroblast growth factor-2), and the like are known as a component that induces differentiation of fibroblasts or mesenchymal stem cells into neuronal cells. These components can be used alone or in combination of two or more. Among these components, EGF and FGF-2 are particularly preferably used.

VEGF, Wnt/β-catenin inhibitors (IWP2, etc.), and the like are known as a component that induces differentiation of fibroblasts or mesenchymal stem cells into cardiomyocytes. These components can be used alone or in combination of two or more. Among these components, VEGF, Wnt/β-catenin inhibitors (IWP2, etc. are particularly preferably used.

Oncostatin M (OsM), DEX, hepatocyte growth factor (HGF), and the like are known as a component that induces differentiation of fibroblasts or mesenchymal stem cells into hepatocytes. These components can be used alone or in combination of two or more. Among these components, OsM, DEX, and HGF are particularly preferably used.

BMP4, VEGF, FGF1, bFGF, SCF, Flt3-L, TPO, GM-CSF, IL-2, IL-4, IL-15, G-CSF, IL-3, IL-6, IL-7, TNF-α, EPO, IGF-II, and the like are known as a component that induces differentiation of fibroblasts or mesenchymal stem cells into blood cells, which however differ depending on the blood cells of interest. These components can be used alone or in combination of two or more.

Examples of the component that induces differentiation of fibroblasts or mesenchymal stem cells into osteocytes include Runx2, Runx3, Dlx5, ATF4, Osx, Smad1, Wnt, Fgf, Hedgehog, Msx2, Twist, AP-1, Tnc, Ncam1, and Pth1h. These components can be used alone or in combination of two or more.

The culture medium may also preferably contain an estrogen receptor antagonist as a differentiation-inducing component in addition to the differentiation-inducing component relevant to the somatic cells of interest, from the viewpoint of improving the direct transdifferentiation efficiency of the present invention. Examples of the estrogen receptor antagonist include tamoxifen, fulvestrant, and mepitiostane. The addition of the estrogen receptor antagonist is particularly preferred when the gene to be introduced is a mutated GLIS1 gene.

The content of the differentiation-inducing component in the culture medium can be an amount known for each component and is not particularly limited. The content of each component is usually from 0.001 μM to 50 μM in the culture medium.

The basal medium to which the differentiation-inducing component can be added is not particularly limited and can be appropriately selected for any purpose. Examples thereof include minimum essential medium (hereinafter, also referred to as "MEM"), Dulbecco's modified Eagle medium (hereinafter, also referred to as "DMEM"), RPMI1640 medium, 199 medium, and F12 medium, containing 5% by mass to 20% by mass of serum.

The culture medium containing the differentiation-inducing component may already be commercially available, and such a commercially available culture medium may be used.

The culture conditions of the step (b) are not particularly limited and can be appropriately selected for any purpose. For example, the culture temperature is approximately 37° C. Examples of the $CO_2$ concentration include approximately 2% to 5%.

Whether or not the somatic cells of interest have been obtained by the culture in the step (b) can be confirmed by detecting a known marker or the like for each somatic cell of interest.

The method for confirming protein expression using such a marker is not particularly limited, and a method known in the art can be appropriately selected. The protein expression can be confirmed by, for example, immunostaining.

The method for confirming gene expression is not particularly limited, and a method known in the art can be appropriately selected. The gene expression can be confirmed by, for example, quantitative PCR.

A second embodiment of the method for direct transdifferentiation of somatic cells into another somatic cells of the present invention includes the following steps (c) and (d):

(c) a step of introducing a GLIS family gene, a mutated GLIS family gene or a gene product thereof and a transcription factor into somatic cells; and (d) a step of culturing the gene-introduced somatic cells in a culture medium containing a growth factor of another somatic cells.

The step (c) of the second embodiment is the same as the step (a) except that a transcription factor in addition to the GLIS family gene is introduced into somatic cells.

The transcription factor used is preferably a transcription factor known to be involved in the induction of differentiation into the somatic cells of interest. For example, for cardiomyocytes, Tbx5, GATA4, Mef2c, Hand2, or the like can be used as such a transcription factor. For hepatocytes, HNF4a, FOXA3, HNF1a, GATA4, TCF-1, SALL4, TGIF1, MAB21L3, ZIC1, EGFLAM, PITX2, NRF1, ZNF281, CTCFL, TP73, TFE3, DLX6, TCF4, or the like can be used. For neuronal cells, NEUROG1, NEUROG2, NEUROG3, NEUROD1, NEUROD2, or the like can be used. For astrocytes, Nfia, Nfib, Sox9, or the like can be used.

The method for introducing such a transcription factor into the somatic cells is the same as the method for introducing the GLIS gene.

The growth factor for use in the step (d) is a growth factor of another somatic cells, and a growth factor known in the art can be used. Examples of the growth factor of cardiomyocytes include FGF, VEGF, BMP, EGF, Nrg, TGF, PGF, and PDGF. Examples of the growth factor of hepatocytes include HGF, EGF, FGF, and IGF. Examples of the growth factor of neuronal cells and glia cells include NGF, EGF, BDNF, NT, HGF, GDNF, FGF, LIF, HIF, PDGF, M-CSF, IGF, VEGF, and BMP. Examples of the growth factor of osteocytes include M-CSF, BMP, TGFβ, RANKL, and FGF. These growth factors can be used alone or in combination of two or more.

The culture in the step (d) of the second embodiment can be performed in the same way as in the step (b) of the first embodiment.

The method for production by direct transdifferentiation of somatic cells into another somatic cells of the present invention can directly produce another somatic cells from somatic cells by transdifferentiation and is therefore advantageous in that the desired somatic cells can be produced without undergoing the iPS cell stage having the risk of tumorigenesis.

The direct transdifferentiation refers to the direct conversion of certain somatic cells into another somatic cells without undergoing the stem cell stage.

The method for production by direct transdifferentiation of somatic cells into another somatic cells of the present invention is a convenient and easily reproducible method including introducing a gene or a gene product thereof into somatic cells, and culturing the gene-introduced cells in a culture medium containing a growth factor or a differentiation-inducing component, and despite this, can efficiently produce the desired somatic cells in a short period of time.

Another embodiment of the present invention can provide an agent for promoting direct transdifferentiation of somatic cells into another somatic cells, including a GLIS family gene, a mutated GLIS family gene or a gene product thereof.

Specifically, as described above, it has been totally unknown that the GLIS family gene, the mutated GLIS family gene or the gene product thereof alone has a function of promoting the direct transdifferentiation of somatic cells into another somatic cells.

The same as above is used as the GLIS family gene, the mutated GLIS family gene or the gene product thereof, and the same as above is preferred.

The agent for promoting direct transdifferentiation of the present invention is particularly useful when the somatic cells are fibroblasts or mesenchymal stem cells and the another somatic cells are selected from the group consisting of adipocytes, neuronal cells, cardiomyocytes, hepatocytes, osteocytes and blood cells. The method for using the agent for direct transdifferentiation of the present invention is also the same as above.

The agent for direct transdifferentiation of the present invention is used in combination with a differentiation-inducing component of the somatic cells or precursor cells of the somatic cells into another somatic cells, as described above. Therefore, an alternative aspect of the somatic cells provides an agent for direct transdifferentiation of somatic cells into another somatic cells including a GLIS family gene, a mutated GLIS family gene or a gene product thereof, and a component that induces differentiation of the somatic cells into another somatic cells. Another aspect can provide an agent for direct transdifferentiation of somatic cells into another somatic cells including a GLIS family gene, a mutated GLIS family gene or a gene product thereof, a transcription factor, and a growth factor of another somatic cells.

In this context, the same as above is used as the GLIS family gene, the mutated GLIS family gene or the gene product thereof, and the same as above is preferred.

The agent for promoting direct transdifferentiation of the present invention is particularly useful when the somatic cells are fibroblasts or mesenchymal stem cells and the another somatic cells are selected from the group consisting of adipocytes, neuronal cells, cardiomyocytes, hepatocytes, osteocytes and blood cells. The method for using the agent for direct transdifferentiation of the present invention is also the same as above.

The agent for direct transdifferentiation of the present invention may be in a form in which the genes or the gene products thereof are divided into separate containers, may be in a form in which the genes or the gene products thereof are placed together in a single container, or may be in a form in which any number of the genes or the gene products thereof are placed together in each container. This agent for direct transdifferentiation can be suitably used as a kit for somatic cell production. This kit for somatic cell production contains at least the agent for direct transdifferentiation and may further contain other components, if necessary.

EXAMPLES

Next, the present invention will be described further specifically with reference to Examples. However, the present invention is not limited to these Examples by any means.

Example 1

In order to test the influence of a GLIS family gene on the induction efficiency of differentiation into various cells, the GLIS1 gene was introduced into human bone marrow-derived mesenchymal stem cells (MSCs) using a lentivirus vector, and an experiment to induce differentiation into each cell type was conducted.

(1) In order to prepare lentivirus, HEK293FT cells (Thermo Fisher Scientific Inc.) cultured in 10% FBS, 1% penicillin/streptomycin, and 10 mL of DMEM medium were seeded at $2\times10^6$ cells to a 60 mm culture dish (TPP Techno Plastic Products AG) and cultured in 4 mL of an antibiotic-free culture medium. 16 hours after seeding, each plasmid loaded with the GLIS1 gene was introduced into the cells using Lipofectamine 2000 (Thermo Fisher Scientific Inc.). 24 hours after the gene introduction, the culture medium was replaced with 3 mL of an antibiotic-containing culture medium, and 48 hours later, a culture medium supernatant was collected. At the time of virus solution collection, a polybrene solution (final concentration: 8 μg/mL) was added after filtration through a 0.45 mm pore size filter (Whatman plc).

(2) MSCs (human bone marrow-derived mesenchymal stem cells, Lonza Group AG) were cultured in 10% FBS, 1% penicillin/streptomycin, and 10 mL of DMEM medium and 24 hours before lentivirus infection, seeded at $1\times10^4$ cells/ well to a 24-well culture plate (TPP Techno Plastic Products AG). 24 hours after seeding, a culture supernatant was completely removed, and 300 μL of the lentivirus solution mentioned above was then added to the cells, which were then cultured at 37° C. in a 5% $CO_2$ incubator. 24 hours after virus solution addition, the culture medium was replaced with 300 μL of a differentiation-induction medium (Promo-Cell GmbH) specific for each cell type. After the replacement, medium replacement was performed every two or three days. 7, 14, or 21 days after the start of differentiation induction, the sample was fixed, then subjected to an immunocytochemical method, and observed under a fluorescence microscope.

Figure 2:
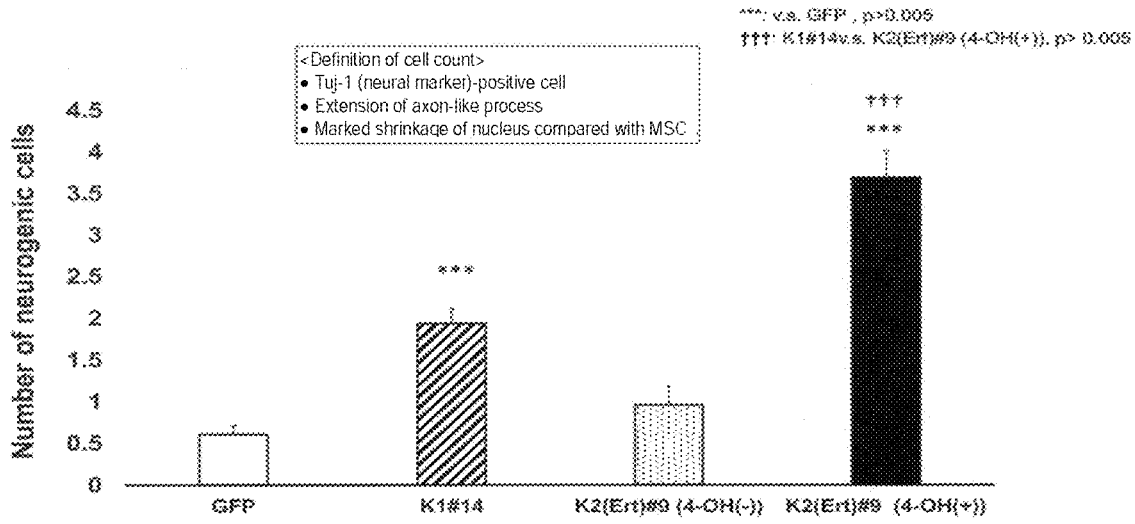
FIG. 2 is a graph showing induction efficiency into neuronal cells after culture for 2 weeks. GFP depicts a control. 1 #14 depicts results of culturing the cells in a culture medium containing a differentiation-inducing component after GLIS1 gene introduction. K2 #9(4-OH(−)) depicts results of culturing the cells in a culture medium containing a differentiation-inducing component after mutated GLIS1 gene introduction. K2(Ert) #9(4-OH(+)) depicts results of culturing the cells in a culture medium containing a differentiation-inducing component and an estrogen receptor antagonist after mutated GLIS1 gene introduction.

(3) The differentiation induction medium used was a culture medium containing components (EGF and FGF-2) that induces differentiation of mesenchymal stem cells into neuronal cells. The neuronal cells were detected according to the criteria: Tuj-1 neural marker-positive cells, extension of an axon-like process, and marked shrinkage of the nucleus compared with MSCs. The results are shown in FIGS. 1 and 2.

Example 2

In order to test the influence of a mutated GLIS family gene on the induction efficiency of differentiation into various cells, the mutated GLIS1 gene was introduced into human bone marrow-derived mesenchymal stem cells (MSCs) using a lentivirus vector, and an experiment to induce differentiation into each cell type was conducted.

(1) In order to prepare lentivirus, HEK293FT cells (Thermo Fisher Scientific Inc.) cultured in 10% FBS, 1% penicillin/streptomycin, and 10 mL of DMEM medium were seeded at $2\times10^6$ cells to a 60 mm culture dish (TPP Techno Plastic Products AG) and cultured in 4 mL of an antibiotic-free culture medium. 16 hours after seeding, each plasmid loaded with the mutated GLIS1 gene (SEQ ID NO: 2) was introduced into the cells using Lipofectamine 2000 (Thermo Fisher Scientific Inc.). 24 hours after the gene introduction, the culture medium was replaced with 3 mL of an antibiotic-containing culture medium, and 48 hours later, a culture medium supernatant was collected. At the time of virus solution collection, a polybrene solution (final concentration: 8 ug/mL) was added after filtration through a 0.45 mm pore size filter (Whatman plc).

(2) MSCs (human bone marrow-derived mesenchymal stem cells, Lonza Group AG) were cultured in 10% FBS, 1% penicillin/streptomycin, and 10 mL of DMEM medium, and 24 hours before lentivirus infection, seeded at $1\times10^4$ cells/well to a 24-well culture plate (TPP Techno Plastic Products AG). 24 hours after seeding, a culture supernatant was completely removed, and 300 μL of the lentivirus solution mentioned above was then added to the cells, which were then cultured at 37° C. in a 5% $CO_2$ incubator. 24 hours after virus solution addition, the culture medium was replaced with 300 μL of a differentiation induction medium (Mesenchymal Stem Cell Adipogenic Differentiation Medium 2 (Ready-to-use) or Mesenchymal Stem Cell Neurogenic Differentiation Medium (Ready-to-use), C-28016, PromoCell GmbH) specific for each cell type. After the replacement, medium replacement was performed every two or three days. 7, 14, or 21 days after the start of differentiation induction, the sample was fixed, then subjected to an immunocytochemical method, and observed under a fluorescence microscope.

(3) The differentiation induction medium used was a culture medium containing a component that induces differentiation of mesenchymal stem cells into neuronal cells (Mesenchymal Stem Cell Neurogenic Differentiation Medium (Ready-to-use), C-28015, PromoCell GmbH). The neuronal cells were detected according to the criteria: Tuj-1 neural marker-positive cells, extension of an axon-like process, and marked shrinkage of the nucleus compared with MSCs. The results are shown in FIGS. 1 and 2.

Example 3

An effect brought about by the addition of an estrogen receptor antagonist was studied.

(1) In order to prepare lentivirus, HEK293FT cells (Thermo Fisher Scientific Inc.) cultured in 10% FBS, 1% penicillin/streptomycin, and 10 mL of DMEM medium were seeded at $2\times10^6$ cells to a 60 mm culture dish (TPP Techno Plastic Products AG) and cultured in 4 mL of an antibiotic-free culture medium. 16 hours after seeding, each plasmid loaded with the GLIS1 gene or the mutated GLIS1 gene (SEQ ID NO: 2) was introduced into the cells using Lipofectamine 2000 (Thermo Fisher Scientific Inc.). 24 hours after the gene introduction, the culture medium was replaced with 3 mL of an antibiotic-containing culture medium, and 48 hours thereafter, a culture medium supernatant was collected. At the time of virus solution collection, a polybrene solution (final concentration: 8 ug/mL) was added after filtration through a 0.45 mm pore size filter (Whatman plc).

(2) MSCs (mesenchymal stem cells, Lonza Group AG) were cultured in 10% FBS, 1% penicillin/streptomycin, and 10 mL of DMEM medium, and 24 hours before lentivirus infection, seeded at $1\times10^4$ cells/well to a 24-well culture plate (TPP Techno Plastic Products AG). 24 hours after seeding, a culture supernatant was completely removed, and 300 μL of the lentivirus solution mentioned above was then added to the cells, which were then cultured at 37° C. in a 5% $CO_2$ incubator. 24 hours after virus solution addition, the culture medium was replaced with an estrogen receptor antagonist (tamoxifen) and 300 L of a differentiation induction medium (PromoCell GmbH) specific for each cell type. After the replacement, medium replacement was performed every two or three days. 7, 14, or 21 days after the start of differentiation induction, the sample was fixed, then subjected to an immunocytochemical method, and observed under a fluorescence microscope.

(3) The differentiation induction medium used was a culture medium containing a component that induces differentiation of mesenchymal stem cells into neuronal cells (Mesenchymal Stem Cell Neurogenic Differentiation Medium (Ready-to-use), C-28015, PromoCell GmbH). The neuronal cells were detected according to the criteria: Tuj-1 neural marker-positive cells, extension of an axon-like process, and marked shrinkage of the nucleus compared with MSCs. The results are shown in FIGS. 1 and 2.

Example 4

(Method for Direct Transdifferentiation of Fibroblasts into Adipocytes)

MSCs (human bone marrow-derived mesenchymal stem cells, Lonza Group AG) were cultured in 10% FBS, 1% penicillin/streptomycin, and 10 mL of DMEM medium, and 24 hours before lentivirus infection, seeded at $1\times10^4$ cells/well to a 24-well culture plate (TPP Techno Plastic Products AG). 24 hours after seeding, a culture supernatant was completely removed, and 300 μL of the lentivirus solution mentioned above was then added to the cells, which were then cultured at 37° C. in a 5% $CO_2$ incubator. 24 hours after virus solution addition, the culture medium was replaced with 300 μL of a differentiation induction medium (Mesenchymal Stem Cell Adipogenic Differentiation Medium 2 (Ready-to-use), C-28016, PromoCell GmbH) specific for each cell type. After the replacement, medium replacement was performed every two or three days. 7, 14, or 21 days after the start of differentiation induction, the sample was fixed, then subjected to an immunocytochemical method, and observed under a fluorescence microscope. The results are shown in FIGS. 3 and 4.

Example 5

(Method for Direct Transdifferentiation into Neuronal Cells, Adipocytes and Osteocytes Using Human Bone Marrow-Derived Mesenchymal Stem Cells (MSCs) (Confirmation by Quantitative PCR)

In order to test the influence of full-length and N-terminally deleted GLIS1 genes on the efficiency of differentiation into various cells, each GLIS1 gene was introduced into human bone marrow-derived mesenchymal stem cells (MSCs) using a lentivirus vector, and an experiment to induce differentiation into each cell type was conducted.

In order to prepare lentivirus, HEK293FT cells cultured in 10% FBS, 1% penicillin/streptomycin, and 10 mL of DMEM medium were seeded at $2\times10^6$ cells to a 60 mm culture dish (TPP Techno Plastic Products AG) and cultured in 4 mL of an antibiotic-free culture medium. 16 hours after seeding, each plasmid loaded with the full-length or N-terminally deleted GLIS1 gene was introduced into the cells using Lipofectamine 2000 (Thermo Fisher Scientific Inc.). 24 hours after the gene introduction, the culture medium was replaced with 7 mL of an antibiotic-containing culture medium, and 48 hours later, a culture medium supernatant was collected. At the time of virus solution collection, a polybrene solution (final concentration: 8 ug/mL) was added after filtration through a 0.45 mm pore size filter (Whatman plc).

MSCs (Lonza Group AG) were cultured in 10% FBS, 1% penicillin/streptomycin, and 10 mL of DMEM medium, and 24 hours before lentivirus infection, seeded at $1 \times 10^4$ cells/well to a 24-well culture plate (TPP Techno Plastic Products AG). 24 hours after seeding, a culture supernatant was completely removed, and 300 uL of the lentivirus solution mentioned above was then added to the cells, which were then cultured at 37° C. in a 5% $CO_2$ incubator. 24 hours after virus solution addition, the culture medium was replaced with 300 uL of a differentiation induction medium (Promo-Cell GmbH) specific for each cell type. After the replacement, medium replacement was performed every two or three days. 7, 14, or 21 days after the start of differentiation induction, the cells were collected, and change in the gene expression of a marker specific for each cell type was studied by use of quantitative PCR.

TABLES 1A and 1B show primers (markers of differentiation-inducing components and the somatic cells of interest) used in the quantitative PCR of the test.

TABLE 1A

| Animal Species | Cell Type | Name of gene | Fw |
|---|---|---|---|
| Human | Neuronal cell | AscI1 | CACTGATTTTGCTGCTGCTTCT (SEQ ID NO: 3) |
| | | Brn2 | GCAAAAGGAAAGCAACTAAGAC (SEQ ID NO: 5) |
| | | Myt1I | TTGTTAAACCTCGGCAAAATCG (SEQ ID NO: 7) |
| | | TUBB3 | GGCCAAGTTCTGGGAAGTCA (SEQ ID NO: 9) |
| | Adipocyte | PPARγ | TCTCAAACGAGAGTCAGCCTTT (SEQ ID NO: 11) |
| | | FABP4 | TACTGGGCCAGGAATTTGAC (SEQ ID NO: 13) |
| | Osteocyte | ALP | CATGCTGAGTGACACAGACAAGAAG (SEQ ID NO: 15) |
| | | BGLAP | CCTCACACTCCTCGCCCTAT (SEQ ID NO: 17) |
| | House-keeping | GAPDH | ATGTTCGTCATGGGTGTGAA (SEQ ID NO: 19) |

Total RNA Extraction: TRIREAGENT (Cosmo Bio Co., Ltd.) 800 μl/1 well
cDNA synthesis: ReverTra Ace® qPCR RT Master Mix with gDNA Remover (Toyobo Co., Ltd.)
Reagent for Q-PCR: THUNDERBIRD® SYBR qPCR Mix (Toyobo Co., Ltd.)
Device for Q-PCR: QuantStudio® 5 real-time PCR system

TABLE 1B

| Animal Species | Cell Type | Name of gene | Rv |
|---|---|---|---|
| Human | Neuronal cell | AscI1 | TGGCGCTCGCGTGTG (SEQ ID NO: 4) |
| | | Brn2 | CCATCTCTCTGTCTCTCTCTC (SEQ ID NO: 6) |
| | | Myt1I | AGACTATTGGAGGTATTGCTGTT CATT (SEQ ID NO: 8) |
| | | TUBB3 | CGAGTCGCCCACGTAGTTG (SEQ ID NO: 10) |

TABLE 1B-continued

| Animal Species | Cell Type | Name of gene | Rv |
|---|---|---|---|
| | Adipocyte | PPARγ | GCAGGCTCCACTTTGATTGC (SEQ ID NO: 12) |
| | | FABP4 | GTGGAAGTGACGCCTTTCAT (SEQ ID NO: 14) |
| | Osteocyte | ALP | TGGTAGTTGTTGTGAGCATAGTCCA (SEQ ID NO: 16) |
| | | BGLAP | TGCTTGGACACAAAGGCTGC (SEQ ID NO: 18) |
| | House-keeping | GAPDH | TGTGGTCATGAGTCCTTCCA (SEQ ID NO: 20) |

Total RNA Extraction: TRIREAGENT (Cosmo Bio Co., Ltd.) 800 μl/1 well
cDNA synthesis: ReverTra Ace® qPCR RT Master Mix with gDNA Remover (Toyobo Co., Ltd.)
Reagent for Q-PCR: THUNDERBIRD® SYBR qPCR Mix (Toyobo Co., Ltd.)
Device for Q-PCR: QuantStudio® 5 real-time PCR system FIG. 5 shows an effect of direct transdifferentiation into neuronal cells using GLIS1. The expression levels of the neuronal cell marker (TUBB3) and the differentiation-inducing component (Brn2) were significantly increased after the GLIS1 gene was introduced into human bone marrow-derived MSCs and the cells were subsequently cultured for 2 weeks using a neurogenic differentiation induction medium (AscI1, Brn2, and Myt1I).

FIG. 6 shows an effect of direct transdifferentiation into adipocytes using GLIS1. The expression levels of the adipocyte marker (FABP4) and the differentiation-inducing component (PPARγ) were significantly increased after the GLIS1 gene was introduced into human bone marrow-derived MSCs and the cells were subsequently cultured for 2 weeks using an adipogenic differentiation induction medium (PPARγ).

FIG. 7 shows an effect of direct transdifferentiation into osteocytes using GLIS1. The expression levels of the osteocyte marker (BGLAP) and the differentiation-inducing component (ALP) were significantly increased after the GLIS1 gene was introduced into human bone marrow-derived MSCs and the cells were subsequently culture for 2 weeks using an osteogenic differentiation induction medium (ALP).

Example 6

(Method for Direct Transdifferentiation of Fibroblasts into Cardiomyocytes by Introducing GLIS1 Gene and Transcription Factor)

In order to test the influence of full-length and N-terminally deleted GLIS1 genes on the efficiency of differentiation into various cells, a cardiomyocyte transcription factor and the full-length or N-terminally deleted GLIS1 gene were introduced into mouse embryonic fibroblasts (MEFs) using a lentivirus vector or a retrovirus vector, and an experiment to induce differentiation into cardiomyocytes was conducted.

In order to prepare each virus for introducing genes, HEK293FT cells or Plat-E cells cultured in 10% FBS, 1% penicillin/streptomycin, and 10 mL of DMEM medium were seeded at $2 \times 106$ cells to a 100 mm culture dish (TPP Techno Plastic Products AG) and cultured in 7 mL of an antibiotic-free culture medium. 16 hours after seeding, plasmids, respectively, loaded with the cardiomyocyte transcription factor and the full-length or N-terminally deleted GLIS1 gene were introduced into the cells using Lipofectamine 2000 (Thermo Fisher Scientific Inc.). 24 hours after the gene introduction, the culture medium was replaced with 7 mL of an antibiotic-containing culture medium, and 48 hours thereafter, a culture medium supernatant was collected. At the time of virus solution collection, a supernatant was collected after centrifugation at 400×g for 10 minutes, and then a polybrene solution (final concentration: 8 ug/mL) was added after filtration through a 45 mm pore size filter (Whatman plc).

MEFs were cultured in 10% FBS, 1% penicillin/streptomycin, and 10 mL of DMEM medium, and 24 hours before virus infection, seeded at 5×104 cells/well to a 24-well culture plate (TPP Techno Plastic Products AG) coated with fibronectin. 24 hours after seeding, a culture supernatant was completely removed, and 500 uL of each virus solution mentioned above was then added to the cells, which were then cultured at 37° C. in a 5% $CO_2$ incubator. 24 hours after virus solution addition, the culture medium was replaced with 500 uL of a cardiomyogenic differentiation induction medium. After the replacement, medium replacement was performed every two or three days. 0, 1, 4, 7, 14, 21, or 28 days after the start of differentiation induction, the cells were collected, and observed under a microscope over time while change in the gene expression of a marker specific for each cell type was studied by use of quantitative PCR.

Table 2 shows plasmids used in Examples 6 to 8.

TABLE 2

| Animal Species | Cell Type | Name of gene | Name of plasmid |
|---|---|---|---|
| Mouse | Cardiomycoyte | MEF2C, GATA4, TBX5 | pMx-puro-MGT |
| | | HAND2 | tetO-Hand2 |
| Human | Cardiomyocyte | MEF2c | tetO-MEF2C |
| | | TBX5 | tetO-TBX5 |
| | | HAND2 | EF1a_HAND_P2A_Hygro_Barcode |
| Human | Cardiomyocyte | GATA4 | EF1a_GATA4_P2A_Hygro_Barcode |
| Mouse | Hepatocyte | | FUW-TetO-Gata4 |
| Mouse | Hepatocyte | HNF4α | pGCDNaam-Hnf4α-IRES-GFP |
| | | FOXA3 | pGCDNaam-Foxa3-IRES-GFP |
| Human | Hepatocyte | HNF1α | EF1a_HNF1A_P2A_Hygro_Barcode |
| | | HNF4α | EF1a_HNF4A_P2A_Hygro_Barcode |
| | | FOXA3 | KF1a_FOXA3_P2A_Hygro_Barcode |
| Mouse | Astrocyte | SOX9 | FUW-TetO-Sox9 |
| | | NFIA | TetO-FUW-NfiA |
| | | NFIB | TetO-FUW-NfiB |

* Those not used at the time of obtainment of the described data are also described.
* Purchased from Addgene TABLES 3A and 3B show primers (markers of transcription factors and the somatic cells of interest) used in the quantitative PCR in Examples 6 to 8.

TABLE 3A

| Animal Species | Cell Type | Name of gene | Fw |
|---|---|---|---|
| Mouse | Cardiomyocyte | SallI | CTCAACATTTCCAATCCG ACCC (SEQ ID NO: 21) |
| | | CTnT | GCGGTAGAACAGTTGACAGAG (SEQ ID NO: 23) |
| | | TBX5 | ATGGCCGATACAGATGAGGG (SEQ ID NO: 25) |
| | Hepatocyte | MAOA | GCCCAGTATCACAGGCCAC (SEQ ID NO: 27) |
| | | GATA4 | CCCTACCCAGCCTACATGG (SEQ ID NO: 29) |

TABLE 3A-continued

| Animal Species | Cell Type | Name of gene | Fw |
|---|---|---|---|
| | Astrocyte | GFAP | GAAACCAACCTGAGGCTGGA (SEQ ID NO: 31) |
| | | NFIA | CCTCCTCTCTCTCCCTCTCG (SEQ ID NO: 33) |
| | House-keeping | GAPDH | AACCTTTGGCATTGTGGAAGG (SEQ ID NO: 35) |

Total RNA Extraction: TRIREAGENT (Cosmo Bio Co., Ltd.) 800 μl/1 well
cDNA synthesis: ReverTra Ace® qPCR RT Master Mix with gDNA Remover (Toyobo Co., Ltd.)
Reagent for Q-PCR: THUNDERBIRD® SYBR qPCR Mix (Toyobo Co., Ltd.)
Device for Q-PCR: QuantStudio® 5 real-time PCR system

TABLE 3B

| Animal Species | Cell Type | Name of gene | Rv |
|---|---|---|---|
| Mouse | Cardiomyocyte | SallI | GGCATCCTTGCTCTTAGTGGG (SEQ ID NO: 22) |

TABLE 3B-continued

| Animal Species | Cell Type | Name of gene | Rv |
|---|---|---|---|
| | | CTnT | CCAGCTCCTTGGTGCTGAT (SEQ ID NO: 24) |
| | | TBX5 | TTCGTGGAACTTGGGGTGTCT (SEQ ID NO: 26) |
| | Hepatocyte | MAOA | CGGGCTTCCAGAACCAAGA (SEQ ID NO: 28) |
| | | GATA4 | ACATATCGAGATTGGGGTGT CT (SEQ ID NO: 30) |
| | Astrocyte | GFAP | CCACATCCATCTCCACGTGG (SEQ ID NO: 32) |
| | | NFIA | GGGGCAGAAGTGCTTCAAT (SEQ ID NO: 34) |
| | Housekeeping | GAPDH | ACACATTGGGGGTAGGAACA (SEQ ID NO: 36) |

Total RNA Extraction: TRIREAGENT (Cosmo Bio Co., Ltd.) 800 µl/1 well cDNA synthesis: ReverTra Ace® qPCR RT Master Mix with gDNA Remover (Toyobo Co., Ltd.)

Reagent for Q-PCR: THUNDERBIRD® SYBR qPCR Mix (Toyobo Co., Ltd.)

Device for Q-PCR: QuantStudio® 5 real-time PCR system

The growth factor-containing culture medium used in Example 6 is as follows.

Basal medium: StemPro-34 SF medium (Gibco, 10639-011) Added reagent/cytokine: GlutaMAX (10 µL/mL, Gibco, 35050-061)

Ascorbic acid (50 µg/mL, Sigma Aldrich, A-4544)

Recombinant human VEGF 165 (5 ng/mL, BioLegend, Inc.)

Recombinant human FGF basic 146 aa (10 ng/mL, BioLegend, Inc.)

Recombinant human FGF 10 (50 ng/mL, BioLegend, Inc.)

Figure 8:
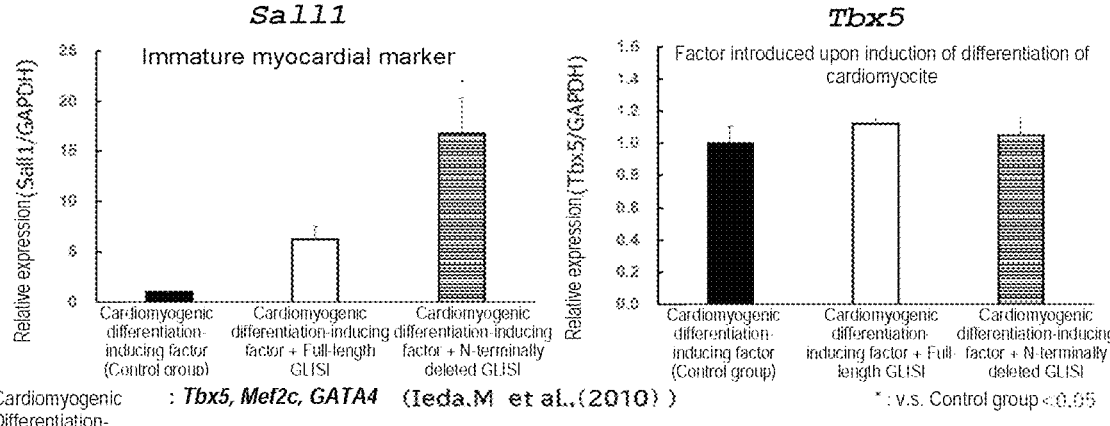
FIG. 8 is graphs showing induction efficiency into cardiomyocytes after culture for 10 days. The left graph shows change in the expression level of an immature cardiomyocyte marker (Sall1). The right graph shows change in the expression level of a cardiomyocyte transcription factor (Tbx5).

FIG. 8 shows an effect of direct transdifferentiation into cardiomyocytes using GLIS1 and cardiomyocyte transcription factors (Tbx5, Mef2c, and GATA4). The expression of the transcription factor (Tbx5) was confirmed and the expression level of the cardiomyocyte marker (Sall1) was significantly increased, after the GLIS1 gene and the cardiomyocyte transcription factors (Tbx5, Mef2c, and GATA4) were introduced into mouse embryonic fibroblasts (P2-3) and the cells were subsequently cultured for 10 days using a cardiomyocyte growth factor-containing culture medium.

Figure 9:
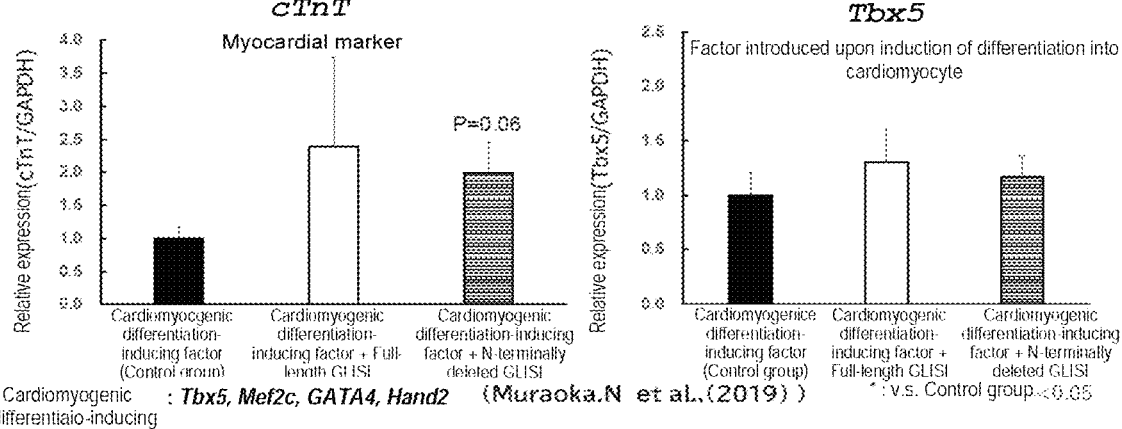
FIG. 9 is graphs showing induction efficiency into cardiomyocytes after culture for 2 weeks. The left graph shows change in the expression level of a cardiomyocyte marker (cTnT). The right graph shows change in the expression level of a cardiomyocyte transcription factor (Tbx5).

FIG. 9 shows an effect of direct transdifferentiation into cardiomyocytes using GLIS1 and cardiomyocyte transcription factors (Tbx5, Mef2c, GATA4, and Hand2). The expression of the cardiomyocyte transcription factor (Tbx5) was confirmed and the expression level of the cardiomyocyte marker (cTnT) was significantly increased, after the GLIS1 gene and the cardiomyocyte transcription factors (Tbx5, Mef2c, GATA4, and Hand2) were introduced into mouse embryonic fibroblasts (P2-3) and the cells were subsequently cultured for 2 weeks using a cardiomyocyte growth factor-containing culture medium.

Example 7

(Method for Direct Transdifferentiation of Fibroblasts into Hepatocytes by Introducing GLIS1 Gene and Transcription Factor)

In order to test the influence of full-length and N-terminally deleted GLIS1 genes on the efficiency of differentiation into various cells, a hepatocyte transcription factor and the full-length or N-terminally deleted GLIS1 gene were introduced into mouse embryonic fibroblasts (MEFs) using a lentivirus vector or a retrovirus vector, and an experiment to induce differentiation into hepatocytes was conducted.

In order to prepare each virus for introducing genes, HEK293FT cells or Plat-E cells cultured in 10% FBS, 1% penicillin/streptomycin, and 10 mL of DMEM medium were seeded at $2 \times 10^6$ cells to a 100 mm culture dish (TPP Techno Plastic Products AG) and cultured in 7 mL of an antibiotic-free culture medium. 16 hours after seeding, plasmids, respectively, loaded with the hepatocyte transcription factor (GATA4) and the full-length or N-terminally deleted GLIS1 gene were introduced into the cells using Lipofectamine 2000 (Thermo Fisher Scientific Inc.). 24 hours after the gene introduction, the culture medium was replaced with 7 mL of an antibiotic-containing culture medium, and 48 hours later, a culture medium supernatant was collected. At the time of virus solution collection, a supernatant was collected after centrifugation at 400×g for 10 minutes, and then a polybrene solution (final concentration: 8 ug/mL) was added after filtration through a 45 mm pore size filter (Whatman plc).

MEFs were cultured in 10% FBS, 1% penicillin/streptomycin, and 10 mL of DMEM medium, and 24 hours before virus infection, seeded at $4.5 \times 104$ cells/well to a 24-well culture plate (TPP Techno Plastic Products AG) coated with gelatin. 24 hours after seeding, a culture supernatant was completely removed, and 500 uL of each virus solution mentioned above was then added to the cells, which were then cultured at 37° C. in a 5% $CO_2$ incubator. 24 hours after virus solution addition, the culture medium was replaced with 500 uL of a medium (1) for hepatocytes. On day 7 of differentiation induction, the cells were reseeded to a 12-well culture plate coated with collagen I, and the culture was continued using a medium (2) for hepatocytes. During the differentiation induction, medium replacement was performed every two or three days. 0, 1, 4, 7, 14, 21, or 28 days after the start of differentiation induction, the cells were collected, and observed under a microscope over time while change in the gene expression of a marker specific for each cell type was studied by use of quantitative PCR.

Medium (1) for hepatocytes (days 1 to 7 of differentiation induction)

Basal medium: DMEM/F12 medium (Gibco)

Added reagent/cytokine: FBS (8%, Gibco)

Penicillin/Streptomycin (1%, Nacalai Tesque, Inc.)

GlutaMAX (10 µL/mL, Gibco, 35050-061)

Nicotinamide (10 mM, Sigma-Aldrich Co. LLC)

Insulin (1 ug/mL, FUJIFILM Wako Pure Chemical Corp.)

β-mercaptoethanol (50 µM, Nacalai Tesque, Inc.)

Dexamethasone (0.1 uM, Sigma-Aldrich Co. LLC)

Medium (2) for hepatocyte (day 7 or later of differentiation induction)

Recombinant human HGF (20 ng/mL, BioLegend, Inc.)

Recombinant human EGF (20 ng/mL, BioLegend, Inc.)

Figure 10:
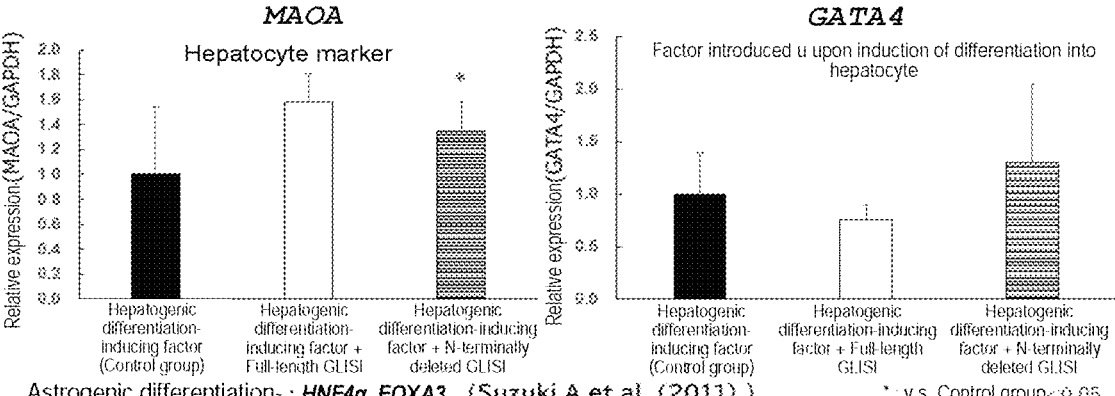
FIG. 10 is graphs showing induction efficiency into hepatocytes after culture for 2 weeks. The left graph shows change in the expression level of a hepatocyte marker (MAOA). The right graph shows change in the expression level of a hepatocyte transcription factor (GATA4).

FIG. 10 shows an effect of direct transdifferentiation into hepatocytes using GLIS1 (full-length and N-terminally deleted GLIS1 genes) and a hepatocyte transcription factor (GATA4). The expression of the hepatocyte transcription factor (GATA4) was confirmed and the expression level of the hepatocyte marker (MAOA) was significantly increased, after the GLIS1 gene and the hepatocyte transcription factor (GATA4) were introduced into mouse embryonic fibroblasts (P2-3) and the cells were subsequently cultured for 2 weeks using a hepatocyte growth factor-containing culture medium.

Example 8

(Method for Direct Transdifferentiation of Fibroblasts into Astrocytes by Introducing GLIS1 Gene and Transcription Factor)

In order to test the influence of full-length and N-terminally deleted GLIS1 genes on the efficiency of differentiation into various cells, an astrocyte transcription factor and the full-length or N-terminally deleted GLIS1 gene were introduced into mouse embryonic fibroblasts (MEFs) using a retrovirus vector, and an experiment to induce differentiation into astrocytes was conducted.

In order to prepare each virus for introducing genes, Plat-E cells cultured in 10% FBS, 1% penicillin/streptomycin, and 10 mL of DMEM medium were seeded at $2 \times 10^6$ cells to a 100 mm culture dish (TPP Techno Plastic Products AG) and cultured in 7 mL of an antibiotic-free culture medium. 16 hours after seeding, plasmids, respectively, loaded with the full-length or N-terminally deleted GLIS1 gene and the astrocyte transcription factor (NFIA) were introduced into the cells using Lipofectamine 2000 (Thermo Fisher Scientific Inc.). 24 hours after the gene introduction, the culture medium was replaced with 7 mL of an antibiotic-containing culture medium, and 48 hours later, a culture medium supernatant was collected. At the time of virus solution collection, a supernatant was collected after centrifugation at 400×g for 10 minutes, and then a polybrene solution (final concentration: 8 ug/mL) was added after filtration through a 45 mm pore size filter (Whatman plc).

MEFs were cultured in 10% FBS, 1% penicillin/streptomycin, and x mL of DMEM medium, and 24 hours before virus infection, seeded at $5 \times 10^4$ cells/well to a 24-well culture plate (TPP Techno Plastic Products AG) coated with gelatin. 24 hours after seeding, a culture supernatant was completely removed, and 500 uL of each virus solution mentioned above was then added to the cells, which were then cultured at 37° C. in a 5% $CO_2$ incubator. 24 hours after virus solution addition, the culture medium was replaced with 500 uL of medium for astrocytes. After the replacement, medium replacement was performed every two or three days. 0, 1, 4, 7, 14, or 21 days after the start of differentiation induction, the cells were collected, and observed under a microscope over time while change in the gene expression of a marker specific for each cell type was studied by use of quantitative PCR.

Medium for Astrocytes
  Basal medium: DMEM (Sigma-Aldrich Co. LLC)
  Added reagent/cytokine: FBS (10%, Gibco)
  Penicillin/Streptomycin 1%, Nacalai Tesque, Inc.)
  β-mercaptoethanol (100 μM, Nacalai Tesque, Inc.)

Figure 11:
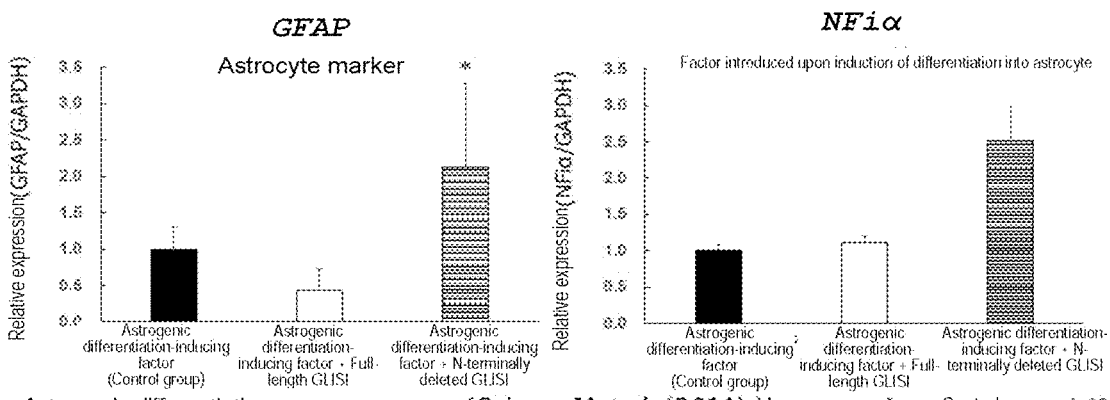
FIG. 11 is graphs showing induction efficiency into astrocytes after culture for 2 weeks. The left graph shows change in the expression level of an astrocyte marker (GFAP). The right graph shows change in the expression level of an astrocyte transcription factor (NFIA).

FIG. 11 shows an effect of direct transdifferentiation into astrocytes using GLIS1 (full-length and N-terminally deleted GLIS1 genes) and an astrocyte transcription factor (NFIA). The expression of the astrocyte transcription factor (NFIA) was confirmed and the expression level of the astrocyte marker (GFAP) was significantly increased, after the GLIS1 gene and the astrocyte transcription factor (NFIA) were introduced into mouse embryonic fibroblasts (P2-3) and the cells were subsequently cultured for 2 weeks using an astrocyte growth factor-containing culture medium.

The invention claimed is:

1. A method for direct transdifferentiation of somatic cells into cardiomyocytes, the method comprising:

(a) introducing (i) a GLIS1 gene, a mutated GLIS1 gene comprising the nucleotide sequence of SEQ ID NO: 2, or a gene product thereof, and (ii) a transcription factor of cardiomyocytes, into somatic cells; and (b) culturing the somatic cells of (a) in a culture medium containing a growth factor of cardiomyocytes, wherein the somatic cells are selected from fibroblasts, mesenchymal stem cells and adipose tissue-derived stromal stem cells, wherein the transcription factor of cardiomyocytes is at least one of Tbx5, GATA4, and Mef2c, and wherein the growth factor of cardiomyocytes is at least one of FGF and VEGF.

2. The method of claim 1, wherein the somatic cells are mesenchymal stem cells.

* * * * *